US009585732B2

(12) United States Patent
Piancino (10) Patent No.: US 9,585,732 B2
(45) Date of Patent: Mar. 7, 2017

(54) ORTHODONTIC DEVICE

(71) Applicant: Maria Grazia Piancino, Turin (IT)

(72) Inventor: Maria Grazia Piancino, Turin (IT)

( * ) Notice: Subject to any disclaimer, the term of this patent is extended or adjusted under 35 U.S.C. 154(b) by 0 days.

(21) Appl. No.: 14/798,362

(22) Filed: Jul. 13, 2015

(65) Prior Publication Data

US 2015/0313688 A1 Nov. 5, 2015

Related U.S. Application Data

(62) Division of application No. 14/354,688, filed as application No. PCT/IB2012/055851 on Oct. 24, 2012.

(30) Foreign Application Priority Data

Oct. 26, 2011 (IT) .............................. TO2011A0971

(51) Int. Cl.
| | |
|---|---|
| *A61C 7/08* | (2006.01) |
| *A61C 7/00* | (2006.01) |
| *A61C 7/10* | (2006.01) |
| *A61F 5/56* | (2006.01) |

(52) U.S. Cl.
CPC .................. *A61C 7/08* (2013.01); *A61C 7/00* (2013.01); *A61C 7/10* (2013.01); *A61F 5/566* (2013.01)

(58) Field of Classification Search
CPC .... A61C 7/00; A61C 7/10; A61C 7/36; A61C 7/08; A61F 5/566
See application file for complete search history.

(56) References Cited

U.S. PATENT DOCUMENTS

| 2,423,005 | A | * | 6/1947 | Chaiken | .................... | A61C 9/00 433/214 |
| 2,708,931 | A | * | 5/1955 | Freedland | ................ | A61B 1/24 128/861 |
| 3,994,068 | A | * | 11/1976 | Goshgarian | .............. | A61C 7/00 433/6 |
| 4,299,568 | A | * | 11/1981 | Crowley | .................. | A61C 7/00 433/6 |
| 4,433,956 | A | * | 2/1984 | Witzig | ..................... | A61C 7/10 433/7 |
| 4,457,708 | A | * | 7/1984 | Dufour | .................... | A61C 7/00 433/6 |

(Continued)

*Primary Examiner* — Cris L Rodriguez
*Assistant Examiner* — Hao D Mai
(74) *Attorney, Agent, or Firm* — Nixon & Vanderhye P.C.

(57) ABSTRACT

Mobile orthodontic device of a functional type comprises a pair of posterior lateral bites (2) in the form of metal plates connected together by means of a metal wire (4). The posterior bites (2) are designed to be set freely floating between the upper dental arch and the lower dental arch. The device also comprise a pair of vestibular shields (3), made, for example, of synthetic material, associated, respectively, to the two posterior lateral bites (2). The device is without palatal plate, so that the metal wire (4) constitutes the only connection between the posterior lateral bites (2). The device can comprise an anterior bite (6) in the form of a metal plate connected to the two vestibular shields (3) through a second metal wire (5). There may moreover be present one or more lateral expansion springs (7), designed to act on the molars, and one or more anterior expansion springs (8), which act on the incisors.

7 Claims, 6 Drawing Sheets

(56) References Cited

U.S. PATENT DOCUMENTS

| | | | | | |
|---|---|---|---|---|---|
| 4,637,796 | A * | 1/1987 | Korn | ............ | A61C 7/00 433/7 |
| 4,723,910 | A * | 2/1988 | Keller | ............ | A61C 7/00 433/7 |
| 4,799,884 | A * | 1/1989 | Bergersen | ............ | A61C 7/08 433/6 |
| 4,802,849 | A * | 2/1989 | Collins, Jr. | ............ | A61C 7/10 433/18 |
| 4,881,896 | A * | 11/1989 | Bergersen | ............ | A61C 7/06 433/5 |
| 5,022,855 | A * | 6/1991 | Jeckel | ............ | A61C 7/00 433/18 |
| 5,096,416 | A * | 3/1992 | Hulsink | ............ | A61C 7/08 433/6 |
| 5,194,003 | A * | 3/1993 | Garay | ............ | A61J 7/0092 433/215 |
| 5,415,542 | A * | 5/1995 | Kesling | ............ | A61C 7/08 433/6 |
| 5,607,300 | A * | 3/1997 | Tepper | ............ | A61C 7/00 433/24 |
| 5,836,761 | A * | 11/1998 | Belvedere | ............ | A63B 71/085 128/861 |
| 5,865,619 | A * | 2/1999 | Cross, III | ............ | A61F 5/566 433/6 |
| 5,879,155 | A * | 3/1999 | Kittelsen | ............ | A63B 71/085 128/861 |
| 6,074,207 | A * | 6/2000 | Coats | ............ | A61C 7/00 433/18 |
| 6,435,871 | B1 * | 8/2002 | Inman | ............ | A61C 7/00 433/21 |
| 6,450,167 | B1 * | 9/2002 | David | ............ | A61C 7/08 128/848 |
| 6,626,665 | B1 * | 9/2003 | Keles | ............ | A61C 7/00 433/18 |
| 6,790,036 | B2 * | 9/2004 | Graham | ............ | A61C 7/08 128/859 |
| 7,581,542 | B2 * | 9/2009 | Abramson | ............ | A61F 5/566 128/848 |
| 8,448,282 | B2 * | 5/2013 | Stapelbroek | ............ | A61C 7/08 15/167.2 |
| 8,517,726 | B2 * | 8/2013 | Kakavand | ............ | A61C 7/08 433/18 |
| 2003/0224311 | A1 * | 12/2003 | Cronauer | ............ | A61C 7/08 433/6 |
| 2004/0265769 | A1 * | 12/2004 | Inman | ............ | A61C 7/00 433/21 |
| 2007/0037110 | A1 * | 2/2007 | Mailyan | ............ | A61C 7/10 433/6 |
| 2007/0184398 | A1 * | 8/2007 | Cronauer | ............ | A61C 7/08 433/6 |
| 2009/0159089 | A1 * | 6/2009 | Jansheski | ............ | A61F 5/566 128/861 |
| 2010/0147315 | A1 * | 6/2010 | Chodorow | ............ | A61F 5/566 128/861 |
| 2011/0195370 | A1 * | 8/2011 | Griffiths | ............ | A61C 7/00 433/6 |
| 2012/0129117 | A1 * | 5/2012 | McCance | ............ | A61C 7/10 433/7 |
| 2013/0122444 | A1 * | 5/2013 | Griffiths | ............ | A61C 7/08 433/6 |
| 2014/0093834 | A1 * | 4/2014 | Andary | ............ | A61F 5/566 433/6 |
| 2016/0081767 | A1 * | 3/2016 | Metcalf | ............ | A61C 7/08 433/6 |

* cited by examiner

ORTHODONTIC DEVICE

This application is a divisional of U.S. application Ser. No. 14/354,688 filed on Apr. 28, 2014, which is the U.S. national phase of International Application No. PCT/IB2012/055851 filed 24 Oct. 2012, which designated the U.S. and claims priority to IT TO2011A000971 filed 26 Oct. 2011, the entire contents of each of which are hereby incorporated by reference.

Forming the subject of the present invention is an orthodontic device, in particular an orthodontic device of a functional or functionalizing type. By "functional devices" is meant those orthodontic devices that, in order to develop forces on the teeth or on the maxillar muscles, exploit in part the muscle tone or modify balancing between the muscles external and internal to the dental arches.

Orthodontic devices, and in particular functionalizing orthodontic devices are used for correction of the malocclusions and for the dentofacial dysformoses. Said devices achieve an orthodontic effect, i.e., an effect linked to the movement of the teeth, and also an orthopaedic effect, in so far as they rebalance and guide the growth of the bone bases on which the teeth are anchored.

Functionalizing devices, as opposed to fixed devices used for treating misalignments, are principally used in orthognathodontics for modifying bad habits and incorrect functions during childhood and adolescence.

Functional devices have a favourable effect on growth and development of the dental arches and the jaws, acting both on the bone component and on the muscular component. They have a cost generally lower than that of fixed braces, are prepared directly in the laboratory, and do not require particular equipment for adjustment and adaptation thereof. A major advantage of functional devices is that they do not create difficulties as regards oral hygiene since they do not anchor to the teeth and are removed during meals.

Known in the art are orthodontic device, which comprise at least one pair of posterior lateral bites in the form of a metal plates provided with means for mutual connection, designed to be set freely floating between the upper dental arch and the lower dental arch, and a pair of vestibular shields, made, for example, of synthetic material, associated, respectively, to the two posterior lateral bites. The means for connection of the posterior lateral bites are constituted by at least one metal wire that connects together the two vestibular shields, or directly the two posterior lateral bites.

The vestibular shields intercept the masticatory muscles and muscles of the cheeks during swallowing (deglutition of saliva); the movements of these muscles develop forces that through the orthodontic device are transmitted to the teeth.

Orthodontic devices of this type are completely free devices, i.e., they are not fixed in any way to the teeth, are free to move between the upper dental arch and the lower dental arch, and render the mandible free to reposition itself in space improving the functionality of the temporomandibular articulation.

Current orthodontic device further comprise a palatal plate, i.e., an element made of resin shaped on the mould of the palate of the patient using the device.

The palatal plate is obtained starting from the mould of the hollow of the palate of the patient. The presence of the palatal plate thus renders said type of devices not suitable for industrial mass production. This of course has a repercussion also on the final cost of said devices and on production times given that they must be made individually and personalized on the anatomical characteristics of the patient. Moreover, in the case where the braces are designed for a small child, the operation of making the mould of the palate is difficult and problematical.

The object of the present invention is to provide orthodontic device of the type specified above that will enable to overcome the above referred drawbacks.

The aim of the present invention is moreover to achieve said result with orthodontic device having a relatively simple and low-cost structure, which will in particular be simple and fast to produce, albeit keeping unaltered the characteristics of functionality of the device itself.

In order to achieving said purposes, forming the subject of the present invention are orthodontic device of the above referred type, characterized in that the devices are without the palatal plate so that the aforesaid at least one metal wire constitutes the only connection between the posterior lateral bites.

Preferably, the orthodontic device according to the invention further comprise an anterior bite in the form of a metal plate, designed to be set freely floating between the upper dental arch and the lower dental arch in a position corresponding to the incisors.

Moreover, in a preferred embodiment of the orthodontic device the anterior bite is fixed to a second metal wire that connects together either the two vestibular shields, or alternatively the two posterior lateral bites.

The anterior bite may be a single bite in the form of a metal plate or else a double bite comprising two metal plates set above one another and at a distance apart, joined together in a central portion so as to bestow elastic properties thereon.

In some embodiments, there may be provided one or more lateral expansion springs, which are connected directly to the vestibular shields and are designed to act on the molars. In addition, some more complete embodiments also comprise one or more anterior expansion springs, which are designed to act on the incisors and are carried preferably by the aforesaid lateral expansion springs.

Finally, in some embodiments the vestibular shields are asymmetrical.

Thanks to the aforesaid characteristics, the orthodontic device according to the invention enable all the favourable characteristics of excellent functionality to be maintained, at the same time rendering simpler and less costly their production, hence overcoming the drawbacks set forth above.

Further characteristics and advantages of the invention will emerge from the ensuing description with reference to the annexed drawings, which are provided purely by way of non-limiting example and in which.

The drawings show, purely by way of non-limiting example, different embodiments of mobile orthodontic device according to the present invention. It is evident that the details of construction of said orthodontic devices that are described herein for completeness, could be obtained in any other known way, without prejudice to the fact that the principle of the invention lies in the absence of the palatal plate and in the fact that the metal wire constitutes the only element of connection between the two posterior lateral bites.

With reference now to the example represented in the drawings, the reference number 1 designates as a whole a removable orthodontic device of a functional or functionalizing type. The device comprise a pair of posterior lateral bites 2 in the form of metal plates connected together by means of a metal wire 4. The two posterior lateral bites 2 are designed to be set freely floating between the upper dental arch and the lower dental arch, and in particular at the height of the molar teeth. During use of the device, the two metal plates 2, which are substantially rectangular and have rounded edges, are set between the upper molars and the lower molars and prevent them from bearing upon one another. In particular, the metal plates 2 come into contact with the portion of the molar occlusal table.

Associated to each posterior lateral bite 2 is a vestibular shield 3 made of synthetic material, such as for example resin. In particular, with reference to the embodiments illustrated in the drawings, a longitudinal end portion 2a of the metal plate 2 is received and embedded in the synthetic material that constitutes the vestibular shield 3. The vestibular shields 3, in the form of a cushion, on one side face the internal wall of the cheeks and during swallowing intercept the movements of the internal muscles (the masseter or the masticatory muscles), and on the other come into contact with the external walls of the molar teeth.

The two posterior metal bites 2 are connected together by a metal wire 4, normally made of steel. In the embodiments illustrated in the drawings, in actual fact the metal wire 4 connects the two vestibular shields 3 together. Alternatively, in one embodiment not illustrated in the figures, the metal wire 4 connects directly the two posterior lateral bites 2 together.

In the embodiment illustrated in the figures, the terminal portions 4a and 4b of said metal wire 4 are received and withheld within the vestibular shields 3. The metal wire 4 is shaped so as to reproduce the curvature of the upper arch and is shaped to fit in the hollow between the upper lip and the external wall of the upper teeth. Preferably, said wire 4 has in its portions close to the vestibular shields two curved portions 4c set apart from one another. The curved portions 4c enable the wire 4 to be more elastic and adjustable to adapt to the morphological structure of the patient.

In the absence of the palatal plate, the metal wire 4 constitutes the only element of connection between the two posterior lateral bites 2.

Figure 2:
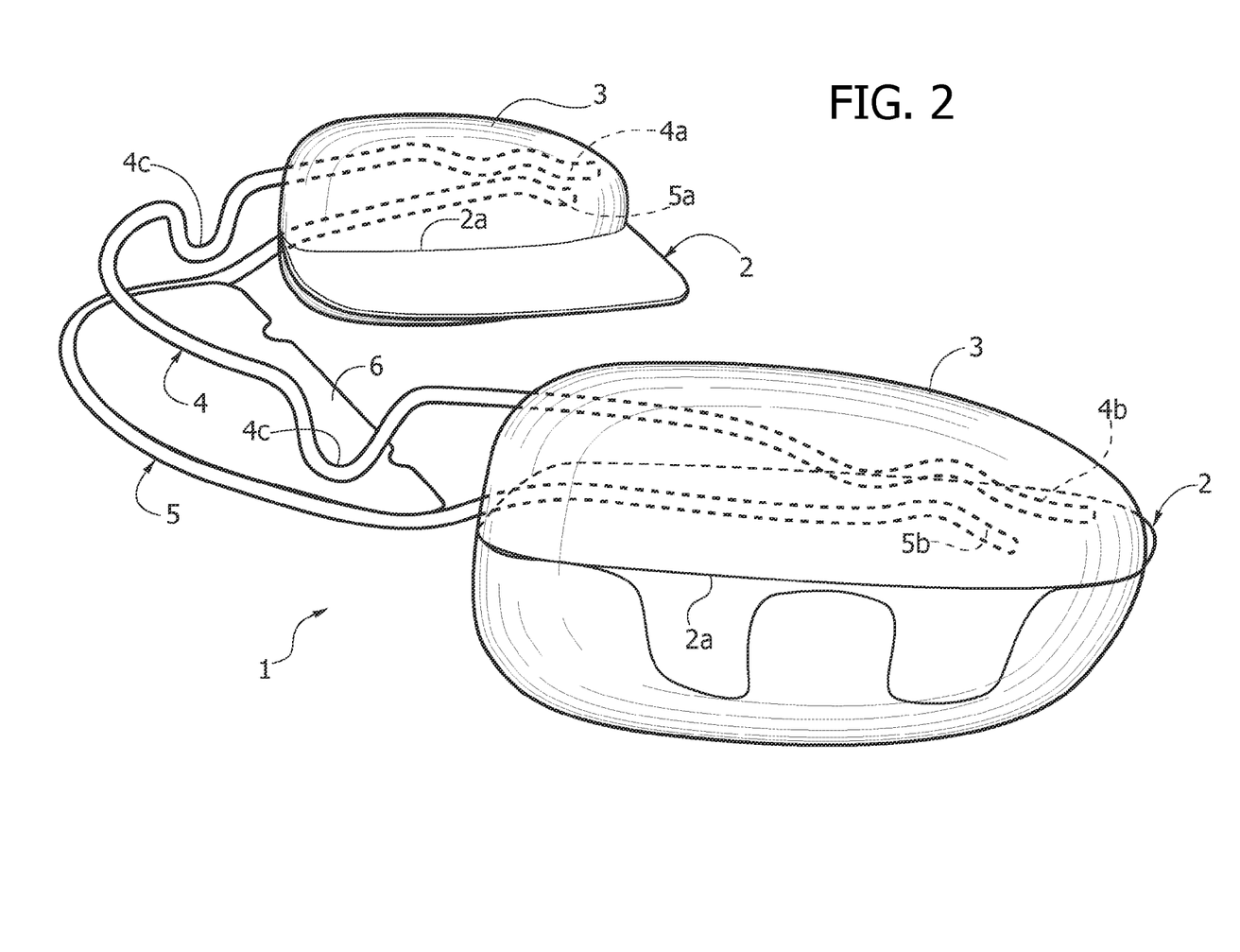
FIGS. 2 to 6 are further examples of embodiment of the orthodontic device of FIG. 1.

With reference to FIG. 2, the orthodontic device also comprise an anterior bite 6 in the form of a metal plate, designed to be set freely floating between the upper dental arch and the lower dental arch in a position corresponding to the incisors. In the embodiment illustrated in FIG. 2, the anterior bite 6 is connected to the two vestibular shields 3 through a second metal wire 5. The ends 5a and 5b of said metal wire are also embedded in the vestibular shields 3.

Figure 3:
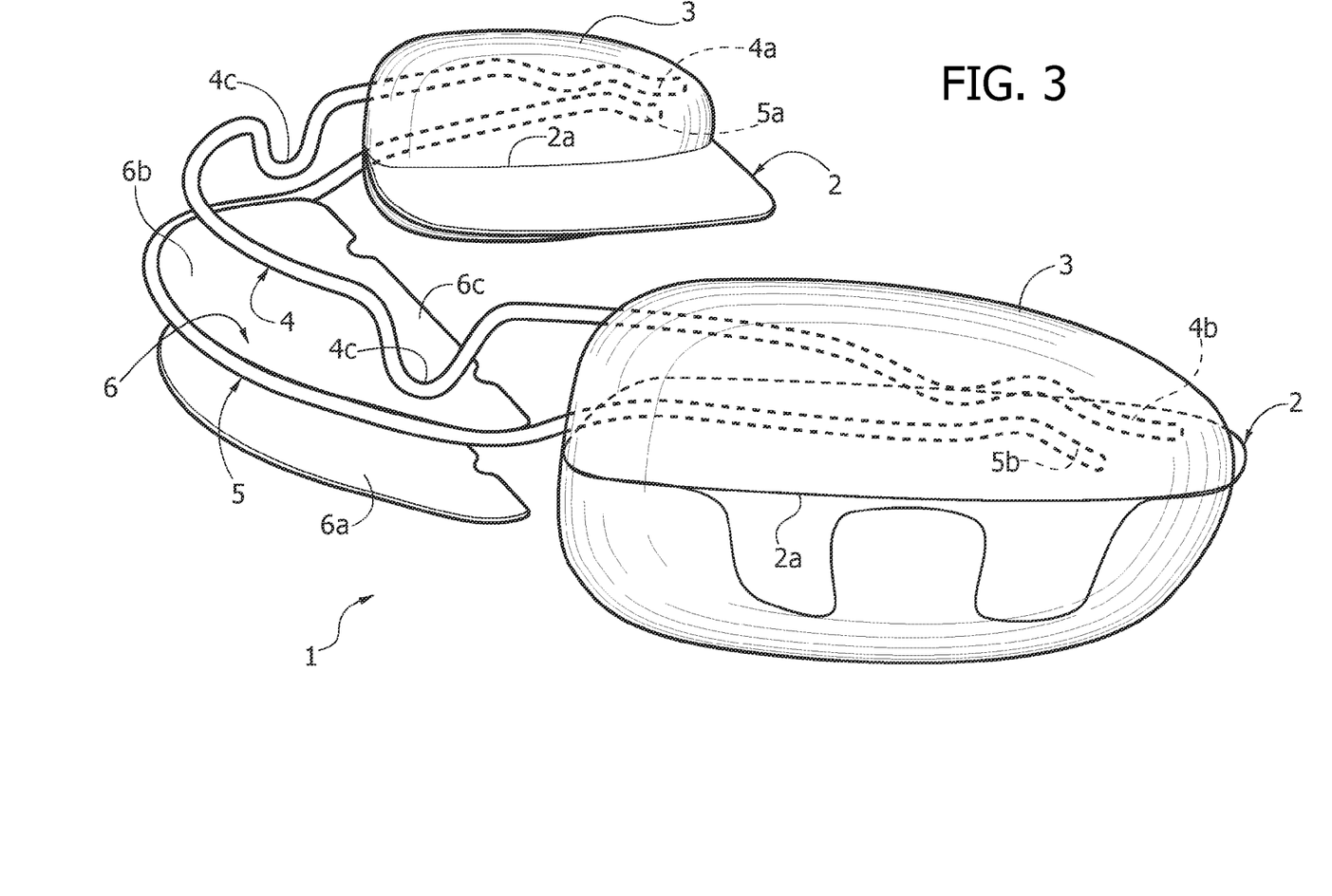

With reference to FIG. 3, in an alternative embodiment the anterior bite 6 is of a double type comprising two metal plates 6a and 6b set above one another and at a distance apart and joined together in a central portion by a bent back portion 6c. The two metal plates 6a and 6b are substantially semicircular in shape. The two metal plates are joined together in the central portion of the diameter. The bent back portion 6c bestows elastic properties on the anterior bite 6. Moreover, the bent back portion 6c has a width smaller than the overall diameter of the plates 6. The bottom plate 6a in use comes into contact with the teeth of the lower arch whilst the plate 6b comes into contact with the teeth of the upper arch. The double bite is generally made of a single piece by moulding, and subsequently bent back to bestow on it the shape represented in the drawings.

Figure 4:
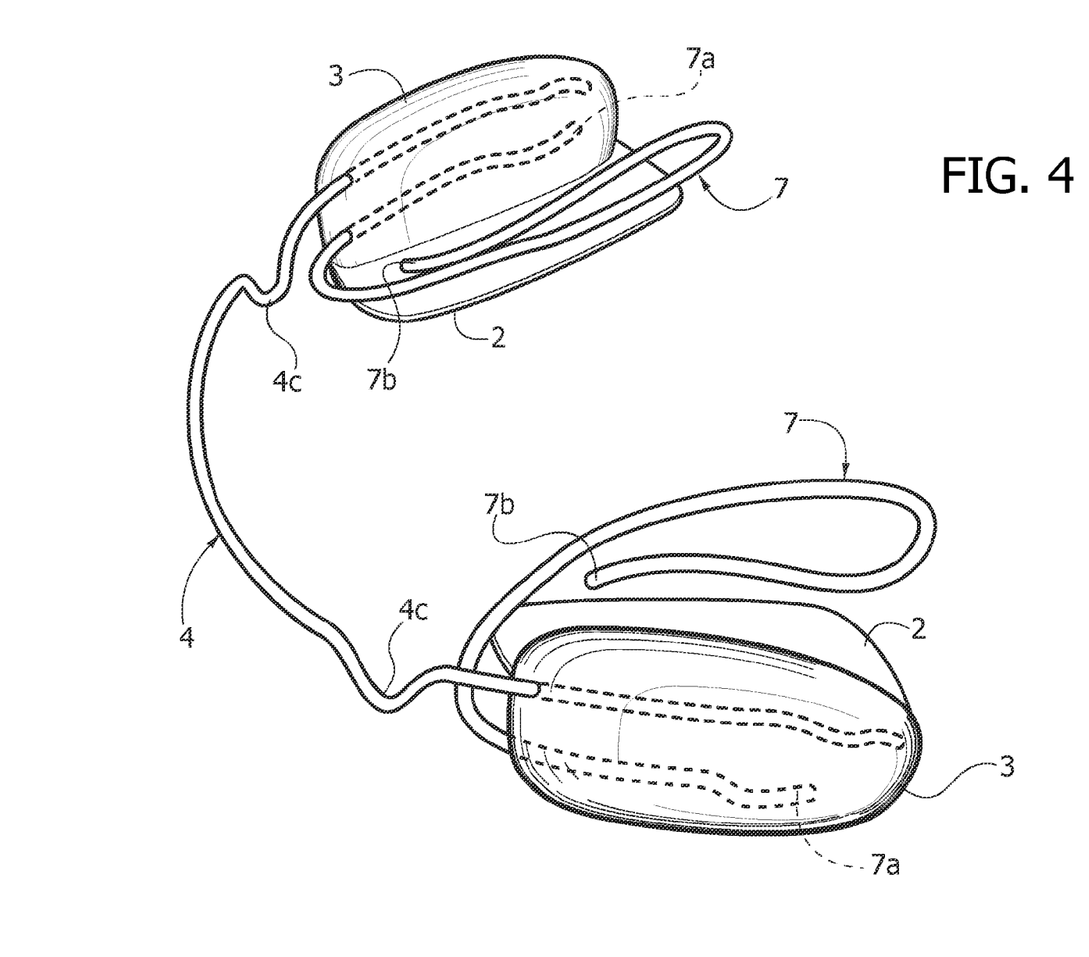
Figure 5:
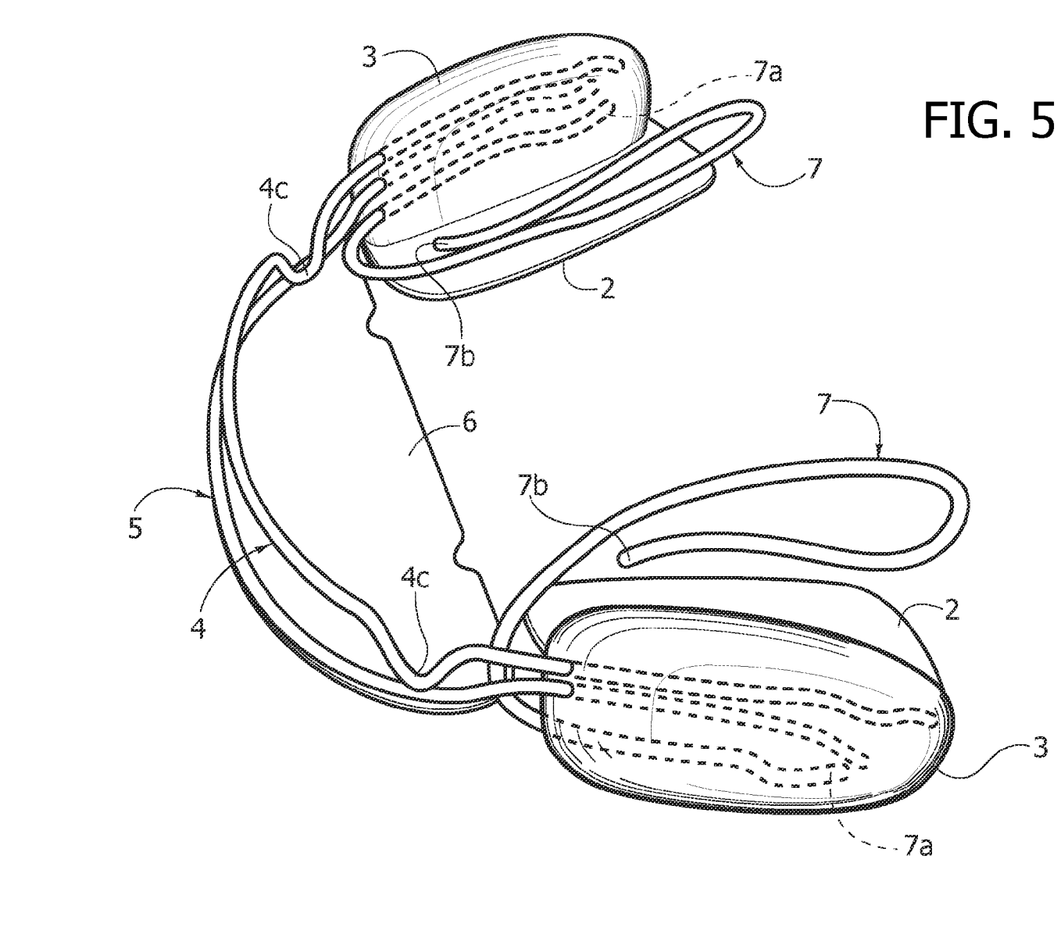

With reference to FIG. 4, the orthodontic device can moreover comprise two lateral expansion springs 7. The expansion springs 7 are metal wires bent back that are designed to act on the molars exerting a slight pressure thereon. One end 7a of the springs 7 is directly connected to the vestibular shields 3, whilst the other end 7b is free.

Figure 6:
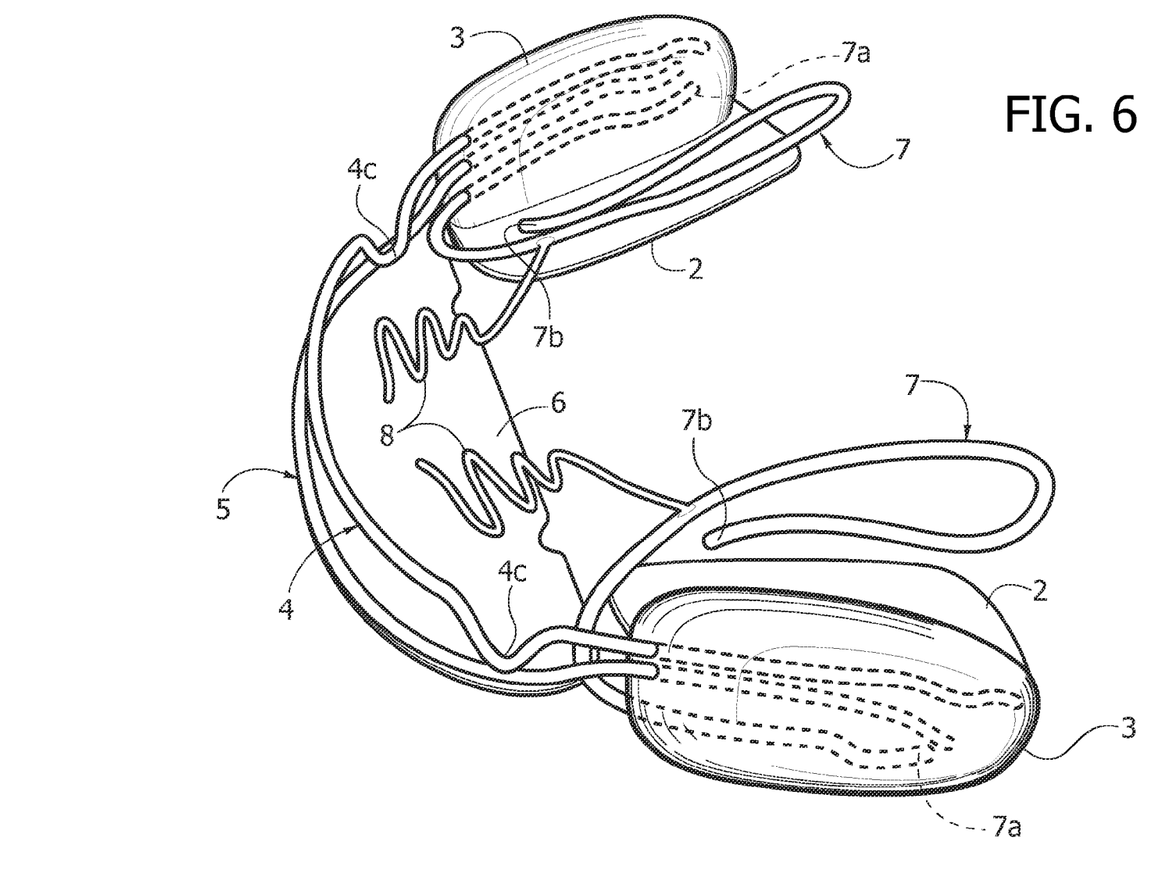

In the embodiment illustrated in FIG. 6, there are also present two anterior expansion springs 8, designed to act on the incisors. The anterior springs 8 in the embodiment illustrated in FIG. 6 are directly connected to the aforesaid lateral expansion springs 7.

Finally, in one embodiment (not illustrated) the vestibular shields 3 can be asymmetrical so as to generate different forces on the two sides of the mouth of the patient.

Figure 1:
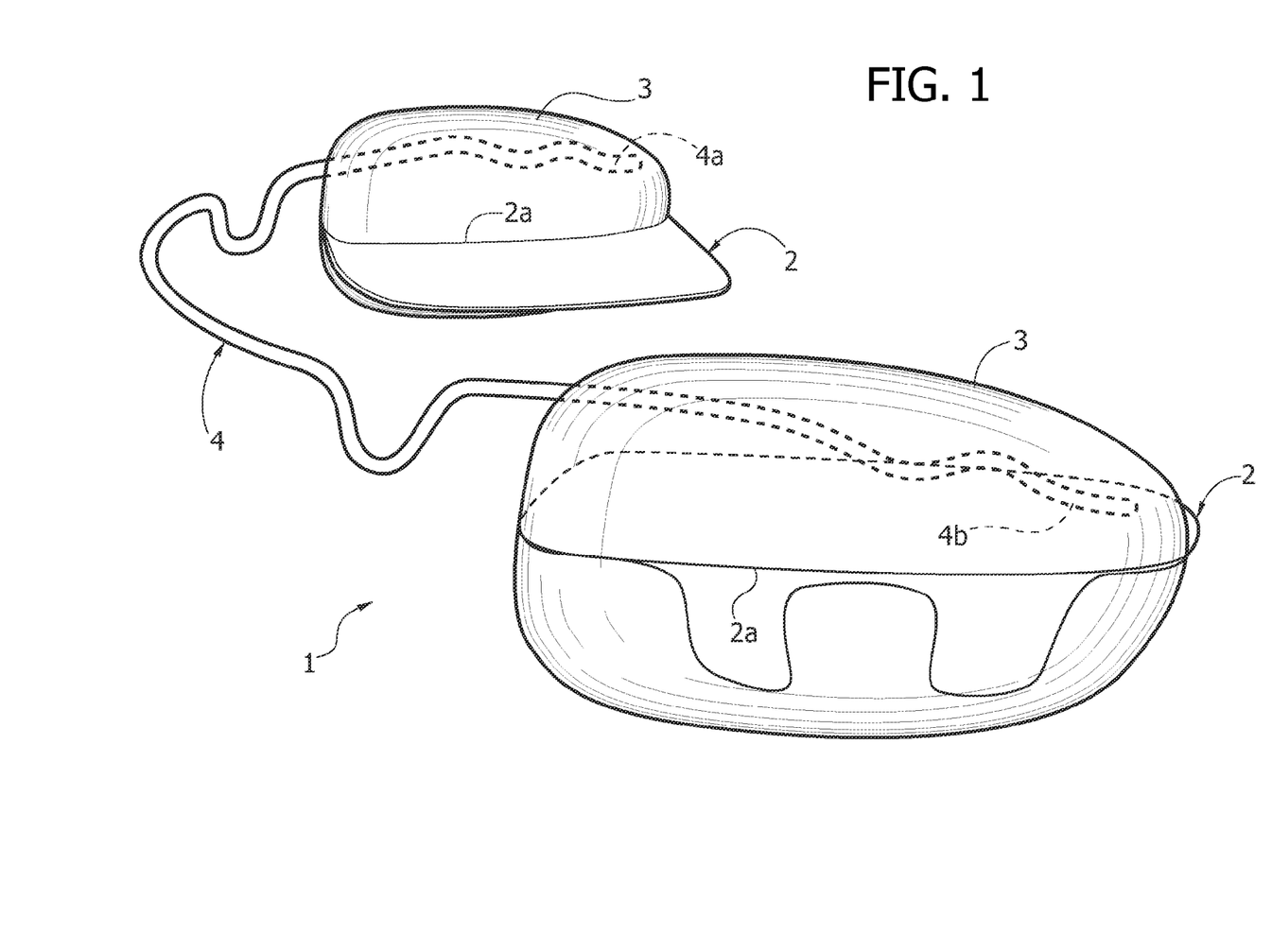
FIG. 1 is a perspective view of an example of embodiment of the orthodontic device according to the present invention, in its basic form.

Thanks to the conformation of the orthodontic device according to the invention, the aforesaid drawbacks are all amply overcome. The embodiments vary with respect to one another starting from a more essential form illustrated in FIG. 1 to arrive at a more complete form (illustrated in FIG. 6).

Of course, without prejudice to the principle of the invention, the details of construction and the embodiments may vary, even significantly, with respect to what has been illustrated herein purely by way of non-limiting example, without thereby departing from the sphere of protection of the invention, said sphere of protection being defined by the annexed claims.

The invention claimed is:

1. A method of installing an orthodontic device in a person's mouth, wherein the device comprises:
   two posterior lateral bites, each in the form of a metal plate provided with means for connection to one another, said two posterior lateral bites are configured to be set freely floating between an upper dental arch and a lower dental arch,
   two vestibular shields made of synthetic material, each connected to each of the two posterior lateral bites, said two vestibular shields each is configured to be positioned between the person's cheek and molar teeth,
   said means for connection of the posterior lateral bites comprising two wires and an anterior bite, which connect together either the two vestibular shields or directly the two posterior lateral bites,
   two lateral expansion springs, each is directly connected to each of the two vestibular shields,
   wherein the two lateral expansion springs, each comprises a bent back metal wire having one end directly connected to one of the respective vestibular shields and another end being free,
   wherein said device is without a palatal plate so that said two wires and the anterior bite are the only connection between said vestibular shields or posterior lateral bites, and
   wherein the method comprises:
      selecting the device,
      installing the device in the person's mouth such that the posterior lateral bites are freely floating between the person's upper dental arch and lower dental arch in a position corresponding to the person's molar teeth and the device has no rigid connection to the person's upper dental arch or lower dental arch, and
      wherein the two lateral expansion springs' bent back metal wires exert a slight pressure on the person's molar teeth.

2. The method according to claim 1, wherein the anterior bite is in the form of a metal plate, that freely floats between the person's upper dental arch and lower dental arch in a position corresponding to the person's incisors.

3. The method according to claim 2, wherein the anterior bite is fixed to one of said two wires that connects together either the two vestibular shields or the two posterior lateral bites.

4. The method according to claim 2, wherein said anterior bite is a single bite.

5. The method according to claim 2, wherein said anterior bite is a double bite comprising two metal plates set above one another and at a distance apart, joined together in a bent-back central portion so as to bestow elastic properties on the anterior bite.

6. The method according to claim 1, wherein the device comprises one or more anterior expansion springs, which are designed to act on the person's incisors and are carried by the lateral expansion springs.

7. The method according to claim 1, wherein said vestibular shields are asymmetrical.

* * * * *